United States Patent [19]

Spillert et al.

[11] Patent Number: 4,661,478
[45] Date of Patent: Apr. 28, 1987

[54] PROCESS FOR POTENTIATING EFFECTS OF BARBITUATE ANESTHESIA TO A WARM-BLOODED ANIMAL

[75] Inventors: Charles R. Spillert, West Orange, N.J.; Corinne Devereux, Bronxville, N.Y.; Eric J. Lazaro, Jersey City, N.J.

[73] Assignee: University of Medicine and Dentistry of New Jersey, Newark, N.J.

[21] Appl. No.: 655,080

[22] Filed: Sep. 27, 1984

[51] Int. Cl.$^4$ ............... A61K 31/635; A61K 31/515; A61K 31/505
[52] U.S. Cl. .................................... 514/158; 514/270; 514/275
[58] Field of Search .............. 424/229, 257; 514/158, 514/275, 270

[56] References Cited

U.S. PATENT DOCUMENTS 4,303,643 12/1981 Armstrong ...................... 424/229

*Primary Examiner*—Jerome D. Goldberg
*Attorney, Agent, or Firm*—Weiser & Stapler

[57] ABSTRACT

There is disclosed a process for treating a warm-blooded animal subjected to barbituate anesthesia to potentiate effects thereof wherein there is administered to the warm-blooded animal a therapeutically effective amount of a composition selected from the group consisting of 5-methyl-3-sulfanilamidoisoxazole, a salt of 5-methyl-3-sulfanilamidoisoxazole with a pharmaceutically acceptable base, 2,4-diamino-5-3-(3,4,5-trimethoxybenzyl) pyrimidine, a salt of 2,4-diamino-5-(3,4,5-trimethoxybenzyl) pyrimidine with a pharmaceutically acceptable acid and mixtures thereof.

8 Claims, No Drawings

PROCESS FOR POTENTIATING EFFECTS OF BARBITUATE ANESTHESIA TO A WARM-BLOODED ANIMAL

FIELD OF THE INVENTION

This invention relates to barbituate anesthesia, and more particularly to a process for potentiating the effects of barbituate anesthesia to a warm-blooded animal.

BACKGROUND OF THE INVENTION

In U.S. Pat. No. 2,909,522, there is disclosed 2,4-diamino-5-(3,4,5-trimethoxybenzyl)pyrimidine and a process for preparing same. In U.S. Pat. No. 2,888,455, there is disclosed 5-methyl-3-sulfanilamidoisoxazole and a process for preparing same. In U.S. Pat. No. Re. 28,636 there is disclosed a therapeutically active antibacterial composition comprising 5-methyl-3-sulfanilamidoisoxazole, or a salt thereof together with a pharmaceutically acceptable base and 2,4-diamino-5-(3,4,5-trimethoxybenzyl)pyrimidine or a salt thereof with a pharmaceutically acceptable acid.

SUMMARY OF THE INVENTION

To a warm-blooded animal subjected to barbituate anesthesia there is administered a therapeutically effective amount of a composition selected from the group consisting of 5-methyl-3-sulfanilamidoisoxazole, a salt of 5-methyl-3-sulfanilamidoisoxazole with a pharmaceutically acceptable base, 2,4-diamo-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof.

DETAILED DESCRIPTION OF THE INVENTION

In a most comprehensive embodiment, the present invention relates to a pharmaceutical composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof, useful in potentiating the effects of barbituate anesthesia to a warm-blooded animal.

In a more particular embodiment, the present invention relates to a pharmaceutical composition, in suitable intravenour or oral dosage forms, which composition is selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof, useful in potentiating the effects of barbituate anesthesia to a warm-blooded animal.

The expression "salts thereof with pharmaceutically acceptable bases" utilized throughout the present specification to denote salts of 5-methyl-3-sulfanilamidoisoxazole, preferably includes those formed utilizing an alkali metal base, such as sodium hydroxide, potassium hydroxide, etc.

The expression "salts thereof with pharmaceutically acceptable acids" utilized throughout the present specification to denote salts of 2,4-diamino-5-(3,4,5-trimethoxybenzyl)pyrimidine, preferably includes those formed utilizing mineral acids, such as hydrochloric acid, sulfuric acid, etc.; and organic acids, such as acetic acid, citric acid, lactic acid, maleic acid, salicylic acid, etc.

It is also within the scope of this invention to administer each active component individually. Thus, it is possible to formulate each of the components into separate dosage forms in accordance with procedures hereinbefore and hereinafter described for the combination.

The compositions of this invention are prepared simply by admixing 5-methyl-3-sulfanilamidoisoxazole or a salt thereof with a pharmaceutically acceptable base and 2,4-diamino-5-(3,4,5-trimethoxybenzyl)pyrimidine or a salt thereof with pharmaceutically acceptable acid.

In addition to the therapeutically active ingredients mentioned heretofore, the compositions of this invention can contain, as optional ingredients, any of the various adjuvants which are used ordinarily in the production of pharmaceutical preparations. Thus, for example, in formulating the present compositions into the desired intravenous form, one may use, as optional ingredients, antioxidants such as ascorbic acid. It should be fully understood, however, that the optional ingredients herein named are given by way of example only and that the invention is not restricted to the use hereof. On the contrary, other such adjuvants, the identity and use of which are well known in the art, can be, and are, employed in carrying out this invention.

The ratios in which the therapeutically active components are utilized in the compositions of this invention can be varied within wide limits. For example, the compositions can contain from about 1 to about 30 parts of 5-methyl-3-sulfanilamidoisoxazole or an equivalent amount of salt thereof to about 30 to about 1 part of 2,4-diamino-5-(3,4,5-trimethoxybenzyl)pyrimidine or an equivalent amount of salt thereof, preferably from about 5 to about 15 parts of 5-methyl-3-sulfanilamidoisoxazole or an equivalent amount of a salt thereof to one part of 2,4-diamino-5-(3,4,5-trimethoxybenzyl)pyrimidine or an equivalent amount of salt thereof.

The composition of the present invention can be administered in unit dosage forms which contain 500 mg. of 5-methyl-3-sulfanilamidoisoxazole or an equivalent amount of a salt thereof and from about 25 mg. to about 100 mg. of 2,4-diamino-5-(3,4,5-trimethoxybenzyl)pyrimidine or an equivalent amount of a salt thereof. However, it is also within the scope of this invention to utilize a unit dosage form which will contain from about 250 mg. to about 800 mg. of 5-methyl-3-sulfanilamidoisoxazole or an equivalent amount of a salt thereof and from about 12.5 mg. to about 160 mg. of 2,4-diamino-5-(3,4,5-trimethoxybenzyl)pyrimidine or an equivalent amount of a salt thereof. The frequency with which any such unit dosage form will be administered to a warm-blooded animal will vary, depending upon the quantity of medicament present therein and the needs and requirements of the warm-blooded animal. Under ordinary circumstances, however, about a total of 60 mg./kg. of 5-methyl-3-sulfanilamidoisoxazole and about a total of 8 mg./kg. of 2,4-diamino-5-(3,4,5-trimethoxybenzyl)pyrimidine, in combination, can be administered daily in several doses.

As hereinabove discussed, detailed description is made with reference to unit dosages whether in intravenous or oral form, the frequency and dosage levels are best related with regard to potentiating or modulating effectiveness in terms of component levels in the plasma of the warm-blooded animals being treated of the composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)-pyrimidine with a pharmaceutically acceptable acid and mixtures thereof. Generally, it is preferably desired to maintain in the plasma of the warm-blooded animal a component level of the 5-methyl-3-sulfanilamidoisoxazole or an equivalent amount of the salt thereof of from about 80 to 160, preferably about 110 μg./cc. and/or a component level of the 2,4-diamino-5-(3,4,5-trimethoxybenzyl)pyrimidine or an equivalent amount of the salt thereof of from about 5 to 15, preferably 10 μg./cc.

This invention relates to the invention described in copending application (Ser. Nos. 655,079; 655,277; 655,145; and 655,144) filed on even date herewith, the teachings of which are incorporated) by reference herein.

The foregoing, notwithstanding, it should be fully understood that the dosages set forth herein are exemplary only and they do not, in any extent, limit the scope or practice of the present invention. As indicated hereinbefore, the combination of this invention has unexpectedly been found to be particularly useful in potentiating the effects of barbituate anesthesia to a warm-blooded animal.

The invention will be understood better by reference to the following examples which are given for illustration purdoses and are not meant to limit the invention.

EXAMPLE I

Swiss Webster male mice (n=12/group), 60 gms., were given two different doses of an injectable composition (Trimethoprim 16 mg./cc., Sulfamethoxazole 80 mg./cc.)–0.15 cc. or 0.10 cc. or equivalent volumes of saline IP (controls) after administration of pentobarbital sodium (60 mg./kg.) IP. The results are set forth in the following Table I:

TABLE I

Effect of Injectable Composition (IC)
(Trimethoprim + Sulfamethoxazole) on Sodium
Pentobarbital Anesthesia (60 mg./kg.) in Elderly Mice

| Regimen | Mean Sleeping Time | Increase in Sleeping Time Relative to Saline Treated Controls | Significance |
|---|---|---|---|
| 0.10 cc. Saline (N = 12) | 100.9 Min. | — | — |
| 0.10 cc. IC (N = 12) | 113.2 Min. | 1.2% | NS |
| 0.15 cc. Saline (N = 12) | 84.6 Min. | — | $p < .001$ |
| 0.15 cc. IC (N = 12) | 125.4 Min. | 48.2% | |

EXAMPLE II when the above experiment was carried out using 25 gm. mice and 80 mg./kg. of pentobarbital sodium anesthesia with the data set forth in Table II:

TABLE II

Effect of Injectable Composition (IC)
(Trimethoprim + Sulfamethoxazole) on
Pentobarbital Anesthesia (80 mg./kg.) in Young Mice

| Regimen | Mean Sleeping Time | Increase in Sleeping Time Relative to Saline Treated Controls | Significance |
|---|---|---|---|
| 0.10 cc. Saline (N = 19) | 48.9 Min. | — | — |
| 0.10 cc. IC (N = 17) | 82.1 Min. | 67.7% | $p < .001$ |
| 0.05 cc. IC (N = 23) | 74.7 Min. | 52.8% | $p < .001$ |
| 0.025 cc. IC (N = 16) | 73.1 Min | 49.5% | $p < .05$ |
| 0.01 cc. IC (N = 21) | 61.4 Min. | 25.6% | $p < .001$ |

At such dosages, the Injectable Composition significantly prolonged the sleeping times of the mice.

The results set forth above suggest that the present invention could potentiate the effects of drugs generally, e.g. maintain higher drug levels for a given period of time or permit reduced dosages levels for like effectiveness.

Numerous modifications and variations of the present invention are possible in light of the above teachings and, therefore, within the scope of the appended claims, the invention may be practiced otherwise than as particularly described.

What is claimed is:

1. A process for treating a warm-blooded animal to potentiate the effects of barbiturate anesthesia which comprises administering to said warm-blooded animal
   (a) from about 1 to about 30 parts of a member selected from the group consisting of 5-methyl-3-sulfanilamidoisoxazole and a pharmaceutically acceptable salt of 5-methyl-3-sulfanilamidoisoazole
   (b) from about 30 to about 1 part of a member selected from the group consisting of 2,4-diamino-5-(3,4,5-trimethoxybenzyl)pyrimidine and a pharmaceutically acceptable salt of 2,4-diamino-5-(3,4,5-trimethoxybenzyl)pyrimidine, and
   (c) from 60 to 80 mg/kg of barbiturate anesthesia, said compounds (a) and (b) being administered in an amount effective to potentiate the effects of the barbiturate anesthesia.

2. The process as defined in claim 1 wherein said therapeutically effective amount of the composition comprises from about 250 mg. to about 800 mg. of 5-methyl-3-sulfanilamidoisoxazole or an alkali metal salt thereof with a pharmaceutically acceptable base and from about 12.5 mg. to 160 mg. to 2,4-diamino-5-(3,4,5-trimethoxybenzyl)pyrimidine or a salt thereof with a pharmaceutically acceptable acid.

3. The process as defined in claim 1 wherein a component level in the plasma of the warm-blooded animal of said 5-methyl-3-sulfanilamidoisoxazole or an alkali metal salt thereof with a pharmaceutically acceptable base is maintained at from about 80 to 160 µg./cc.

4. The process as defined in claim 3 wherein said component level is preferably about 110 µg./cc.

5. The process as defined in claim 1 wherein a component level in the plasma of the warm-blooded animal of said 2,4-diamino-5-(3,4,5-trimethoxybenzyl)pyrimidine or a salt thereof with a pharmaceutically acceptable acid is maintained at from about 5 to 15 µg./cc.

6. The process as defined in claim 5 wherein said component level is preferably about 10 µg./cc.

7. The process of claim 1 wherein components (a) and (b) are administered separately.

8. The process of claim 1 wherein components (a) and (b) are administered together.

* * * * *